United States Patent [19]

Hung

[11] Patent Number: 5,196,494

[45] Date of Patent: Mar. 23, 1993

[54] HYDROXY CONTAINING FLUOROVINYL COMPOUNDS AND POLYMERS THEREOF

[75] Inventor: Ming-Hong Hung, Wilmington, Del.

[73] Assignee: E. I. Du Pont de Nemours and Company, Wilmington, Del.

[21] Appl. No.: 802,393

[22] Filed: Dec. 4, 1991

Related U.S. Application Data

[62] Division of Ser. No. 713,948, Jun. 12, 1991, Pat. No. 5,093,446, which is a division of Ser. No. 592,172, Oct. 9, 1990, Pat. No. 5,059,720, which is a division of Ser. No. 473,083, Jan. 31, 1990, Pat. No. 4,982,009.

[51] Int. Cl.$^5$ ............................................. C08F 16/24
[52] U.S. Cl. .................................................... 526/247
[58] Field of Search ......................................... 526/247

[56] References Cited

U.S. PATENT DOCUMENTS 3,544,537 12/1970 Brace ................................. 525/200
4,564,717 1/1986 Ohmori et al. ...................... 568/843

FOREIGN PATENT DOCUMENTS 0075312  3/1983  European Pat. Off. ............ 526/247
0093404 11/1983  European Pat. Off. ............ 526/247
 135917  4/1985  European Pat. Off. .
 199138 10/1986  European Pat. Off. .
0296559 12/1988  European Pat. Off. ............ 526/247
0320940  6/1989  European Pat. Off. ............ 526/247
63-002418  1/1988 Japan .
2269306 11/1990 Japan ................................. 526/247

Primary Examiner—Joseph L. Schofer
Assistant Examiner—N. Sarafim
Attorney, Agent, or Firm—Barbara C. Siegell

[57] ABSTRACT

Novel hydroxy containing fluorovinyl ethers, polymers of hydroxy containing fluorovinyl ethers, copolymers of selected hydroxy containing fluorovinyl ethers, a process for reducing ester containing fluorovinyl compounds to the corresponding alcohol with borohydrides, and a process for polymerizing hydroxy containing fluorovinyl ethers are disclosed.

8 Claims, No Drawings

HYDROXY CONTAINING FLUOROVINYL COMPOUNDS AND POLYMERS THEREOF

This is a division of Ser. No. 07/713,948, filed on Jun. 12, 1991, now U.S. Pat. No. 5,093,446 which is a division of Ser. No. 07/592,172, filed on Oct. 9, 1990, now U.S. Pat. No. 5,059,720 which is a division of Ser. No. 07/473,083, filed on Jan. 31, 1990, now U.S. Pat. No. 4,982,009.

FIELD OF THE INVENTION

A process for reducing ester containing fluorovinyl compounds to the corresponding alcohol with alkali metal borohydrides, selected novel hydroxy containing fluorovinyl ethers, novel polymers of hydroxy containing fluorovinyl ethers, a process for making such polymers and novel copolymers of selected hydroxy containing fluorovinyl ethers are provided.

BACKGROUND OF THE INVENTION

Japanese Patent 88002418 reports the synthesis of 7,7-dihydro-7-hydroxy(perfluoro-3-oxahepten-1) by chlorinating the methyl ester of perfluoro(3-oxa-1-heptenoic acid), reduction of the chlorinated product with $NaBH_4$ to give the corresponding alcohol, and then reaction of the alcohol with zinc metal to regenerate the vinyl ether, which is the desired product. It is reported that this compound can be free radically copolymerized with at least one other fluorinated monomer, and optionally non-fluoroinated monomers, to form useful polymers.

U.S. Pat. No. 4,564,717 reports the synthesis of compounds of the formula $CF_2=CF(CF_2)_m(CH_2)_nOH$ wherein m is an integer from 0 to 10 and n is an integer of 1 to 4. Among the methods of preparation described, is the reduction of the compound $CF_2X^1CFX^2CF_2COOR$ (sic) wherein R is alkyl and $X^1$ and $X^2$ are chlorine or bromine, by various reducing agents including alkali metal borohydrides. The olefin is then produced by dehalogenation of the alcohol with a metal such as zinc. In essence, in both this and the previous reference, the double bond has been "protected" by halogenating it (with chlorine or bromine) before the reduction step, and dehalogenating after the reduction step.

European Patent Application 135,917 discloses copolymers of vinylidene fluoride with a compound of the formula $CF_2=CF(CF_2)_m(CH_2)_nOH$ where m is 0 to 10 and n is 1-4, and optionally another fluorinated termonomer. Polymers of hydroxy containing fluorovinyl ethers are not mentioned.

European Patent Application 199,138 reports preparation and polymerization (with other fluorine containing olefins) of the compound $CF_2=CFO(CF_2CFY))_n(CF_2CF_2CH_2O)_mCF_2CF_2CH_2X$, wherein X is hydrogen or halogen, Y is fluorine or $-CF_3$, m is an integer of 0 to 5 and n is 0, 1 or 2. No mention is made of a hydroxy group being present.

It is one object of the present invention to provide a simplified method for the production of hydroxy containing fluorovinyl compounds by the alkali metal borohydride reduction on the corresponding esters. It is an additional object to conduct the reduction process so protection of the double bond, as by halogenation, is unnecessary.

A further object of the invention is to homopolymerize hydroxy containing fluorovinyl ethers using anionic catalysts. It is an additional object to disclose polymers resulting from the polymerization of hydroxy containing fluorovinyl ethers.

Finally, it is also an objective of this invention to provide certain novel hydroxy containing fluorovinyl ethers and their copolymers with selected monomers.

These and other objects are achieved by the invention disclosed in the below specification and in the appended claims.

SUMMARY OF THE INVENTION

This invention concerns a process for the production of hydroxy containing fluorovinyl compounds, comprising, contacting in a solvent an alkali metal borohydride with a compound of the formula $CF_2=CFR^1CO_2R^2$ wherein $R^1$ is a covalent bond, a perfluoroalkylene group and $-OR^3-$ wherein $R^3$ is a perfluoroalkylene group, and $R^2$ is hydrocarbyl or substituted hydrocarbyl. This invention further concerns hydroxy containing fluorovinyl ethers of the formula $CF_2=CF[OCF_2CF(CF_3)]_n(O)_p(CF_2)_mCH_2OH$ wherein p is 0 or 1, m is 0 to 10 and n is 1 to 20, provided that when m is 0, p is 0, and further provided that when m is greater than 0, p is 1. Also disclosed is a process for polymerizing hydroxy containing fluorovinyl ethers, comprising, contacting a base with one or more hydroxy fluorovinyl ethers of the formula $CF_2=CFOR^4CF_2CH_2OH$, wherein $R^4$ is perfluoroalkylene. A polymer consisting essentially of the repeat formula $-[CF_2CFHOR^4CF_2CH_2O]-$, wherein $R^4$ is perfluoroalkylene. Also disclosed is a copolymer containing the hydroxy containing repeat unit $-[CF_2-CF]-$

wherein p is 0 or 1, m is 0 to 10 and n is 1 to 20, provided that when m is 0, p is 0, and further provided that when m is greater than 0, p is 1, with other selected repeat units.

DETAILS OF THE INVENTION

In accordance with the present invention, there is provided a process for the production of hydroxy containing fluorovinyl compounds, comprising, contacting in a solvent an alkali metal borohydride with a compound of the formula $CF_2=CFR^1CO_2R^2$ wherein $R^1$ is selected from a covalent bond, a perfluoroalkylene group and $-OR^3-$ wherein $R^3$ is a perfluoroalkylene group, and $R^2$ is hydrocarbyl or substituted hydrocarbyl.

By "perfluoroalkylene group" herein is meant a bivalent saturated radical regarded as derived from a perfluorinated alkane by the removal of two fluorine atoms from different carbon atoms. The "perfluoroalkylene group" may also contain oxygen atoms between alkylene segments, to form one or more ether groups in each perfluoroalkylene group.

By "substituted hydrocarbyl" herein is meant any substituent in a hydrocarbyl group that will not interfere with the reduction reaction. However, even substituents that react with the alkali metal borohydrides may be present, provided enough borohydride is added to reduce the ester to the alcohol.

Preferred alkali metal borohydrides are lithium borohydride, sodium borohydride and potassium borohydride. The molar ratio of borohydride to ester is about 0.3 to about 1.2, preferably about 0.4 to about 0.8.

It is preferred that the solvent is an alcohol. Preferred alcohols are methanol and ethanol.

The process is carried out at about $-10°$ to about $+30°$ C., preferably about $0°$ to about $15°$ C. and most preferably about $5°$ to about $10°$ C. External cooling may be needed to maintain the correct temperature.

Any substantial amount of water should be excluded from the reaction, and it is convenient to carry out the reaction under an inert atmosphere such as nitrogen, in order to exclude moisture. Starting materials should be substantially dry. Agitation is preferred during the reaction, and it is preferred if the agitation is vigorous for efficient mixing.

Products may be isolated by standard techniques well known to those skilled in the art, such as distillation. Such techniques are illustrated in the Examples.

Typical procedures for preparing compounds of the formula $CF_2=CFR^1CO_2R^2$ are found U.S. Pat. No. 4,275,226; R. Sullivan in J. Org. Chem., vol. 34, pp. 1841–1844 (1969); U.S. Pat. No. 4,281,092; and U.S. Pat. No. 4,138,426.

In preferred embodiments $R^1$ is $-OR^3-$, wherein $R^3$ is $-(CF_2)_y-$, wherein y is 2 to 10; or $R^1$ is $-OR^3-$ wherein $R^3$ is $-[CF_2CF(CF_3)O]_x(CF_2)_z-$, wherein z is 1 to 10 and x is 1 to 20; or $R^1$ is perfluoroalkylene; or $R^1$ is a covalent bond. In an especially preferred embodiments $R^1$ is $-(CF_2)_q-$ wherein q is 1 to 10; or x is 1 and z is 2. In a preferred embodiment of the process $R^2$ is alkyl, and it is especially preferred if $R^2$ is alkyl in combination with any of the preferred embodiments of $R^1$. Unless otherwise noted, all numerical ranges that refer to chemical formulas herein, represent integers throughout those particular ranges and not fractional values.

The hydroxy containing fluorovinyl compounds produced by the above process are useful as monomers in polymerization, and may be homo- or copolymerized (infra).

Also disclosed are hydroxy containing fluorovinyl ethers of the formula $CF_2=CF[OCF_2CF(CF_3)]_n(O)_p(CF_2)_mCH_2OH$ wherein p is 0 or 1, m is 0 to 10 and n is 1 to 20, provided that when m is 0, p is 0, and further provided that when m is greater than 0, p is 1.

In a preferred embodiment of the hydroxy containing fluorovinyl ethers n is 1 to 5, p is 1 and m is 2 to 10. In the most preferred embodiment n is 1, p is 1 and m is 2.

Also disclosed is a process for polymerizing hydroxy containing fluorovinyl ethers, comprising, contacting a base with one or more hydroxy fluorovinyl ethers of the formula $CF_2=CFOR^4CF_2CH_2OH$, wherein $R^4$ is perfluoroalkylene.

The polymers produced by this process are described below.

The polymerization process is preferably carried out in a solvent, preferably a polar but nonprotic solvent. Such solvents are well known to those skilled in the art, and include, but are not limited to N,N-dimethylformamide, dimethylsulfoxide, N,N-dimethylacetamide, tetrahydrofuran, the glymes, etc. N,N-dimethylformamide is preferred. Protic solvents, particularly those that contain a proton more acidic than the hydroxy group in the hydroxy containing fluorovinyl ethers should be avoided. The solvents, and indeed all starting materials should be substantially free of water.

The base used in the process should be one whose conjugate acid is less acidic than the hydroxy proton in the hydroxy containing fluorovinyl ether. The base should also be at least slightly soluble in the reaction medium, so that reaction may be affected. Such bases are well known to those skilled in the art, and include, but are not limited to alkali metal alkoxides, alkali metal hydrides, amines, etc. Alkali metal alkoxides are preferred, and potassium t-butoxide is especially preferred. The molar ratio of hydroxy containing fluorovinyl ether to base is about 5 to about 100, preferably about 8 to about 50, most preferably about 10 to about 25.

The process is run at a temperature of about $-10°$ to about $+100°$ C., preferably about $0°$ to about $50°$ C., most preferably about $10°$ to about $30°$ C. Agitation of the reaction mass is preferred to mix separate phases.

The product polymers may be isolated by techniques well known to those skilled in the art, such as evaporation of solvent. Such techniques are illustrated in the Examples.

In preferred hydroxy containing fluorovinyl ethers used in the process $R^4$ is $-(CF_2)_s-$, wherein s is 1 to 10; or $R^4$ is $-[CF_2CF(CF_3)O]_t(CF_2)_u-$, wherein u is 1 to 10 and t is 1 to 20. In an especially preferred embodiment t is 1 and u is 1, or s is 2.

A polymer consisting essentially of the repeat formula $-[CF_2CFHOR^4CF_2CH_2O]-$, wherein $R^4$ is perfluoroalkylene.

In preferred polymers $R^4$ is $-(CF_2)_s-$, wherein s is 1 to 10; or $R^4$ is $-[CF_2CF(CF_3)O]_t(CF_2)_u-$, wherein u is 1 to 10 and t is 1 to 20. In an especially preferred embodiment t is 1 and u is 1, or s is 2.

These polymers are useful as lubricants, lubricant precursors, macromonomers and coatings. These polymers are made by the process described immediately above.

A copolymer comprising the hydroxy containing repeat unit

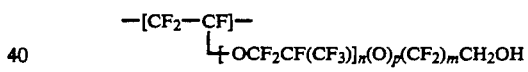

wherein p is 0 or 1, m is 0 to 10 and n is 1 to 20, provided that when m is 0, p is 0, and further provided that when m is greater than 0, p is 1, and one or more other repeat units.

Such a repeat unit, which has a hydroxy contained within it, is useful as a reactive site along the polymer chain to accomplish processes such as crosslinking, or may change the surface characteristics of a polymer while leaving the bulk properties relatively unchanged. Thus in many cases the above repeat unit will be present in the polymer in only relatively small amounts, about 0.001 to about 30 mole percent, preferably about 0.05 to about 15 mole percent.

It is especially useful in crosslinking relatively unreactive polymers, such as fluoropolymers. Thus it can be incorporated into polymers containing repeat units derived from monomers selected from the group consisting of tetrafluoroethylene, hexafluoropropylene and vinylidene hydride; hexafluoropropylene, vinylidene fluoride and tetrafluoroethylene, ethylene and vinylidene fluoride; perfluoro(methyl vinyl ether) and tetrafluoroethylene; perfluoro(methyl vinyl ether) and hexafluoropropylene; chlorotrifluoroethylene; ethylene and chlorotrifluoroethylene; vinylidene fluoride; tetrafluoroethylene and propylene; tetrafluoroethylene and ethylene; tetrafluoroethylene and hexafluoropropylene; perfluoro-2,2-dimethyl-1,3-dioxole; perfluoro-2,2-dimethyl-1,3-dioxole and tetrafluoroethylene; vinyl fluoride; tetrafluoroethylene and perfluoro[2-(fluorosulfonylethoxy)propyl vinyl ether]; and vinyl acetate and tetrafluoroethylene. In the immediately above listing of monomers, each of the monomer(s) between the semicolons represents a specific copolymer of the hydroxy containing fluorovinyl ether with that particular monomer or combination of monomers. By "incorporated into polymers" in the sentence above is meant that when the above polymers (and others not specifically mentioned) are formed by free radical polymerization, the appropriate amount of hydroxy containing fluorovinyl ether monomer is added to the polymerization reaction to be copolymerized with the other monomer(s). It will be noted that the polymers above contain fluoromonomers. The term fluoromonomers means a monomer containing a vinyl group to which at least 1 fluorine atom is directly bound (i.e. has one or more vinylic fluorine atoms). Copolymers of the hydroxy containing fluorovinyl ethers with fluoromonomers, and optionally other monomers, are preferred. Also preferred are copolymers with vinyl esters, and especially preferred is vinyl acetate. Such polymers are useful for example, as molding resins (when plastic) and elastomers (where the "base" polymer is an elastomer).

These copolymers can be made by methods well known to those skilled in the art. Further illustrations of typical polymerizations processes are given in the Examples.

In the following Examples, the following abbreviations and terms are used:

t-BuOK—potassium t-butoxide
dispersion factor—weight average molecular weight/number average molecular weight
DMF—N,N-dimethylformamide
DSC—differential scanning calorimetry
EtOH—ethanol
EVE—methyl perfluoro(4,7-dioxa-5-methylhept-8-enoate)
EVE alcohol—perfluoro(9,9-dihydro-9-hydroxy-3,6-dioxa-5-methylnon-1-ene)
F-113—1,1,2-trichloro-1,2,2-trifluoroethane
GPC—gel permeation chromatography
PDD—perfluoro(2,2-dimethyl-1,3-dioxole) (Can be made by methods described in U.S. Pat. Nos. 3,865,845, 3,978,030 and 4,393,227)
PMMA—poly(methyl methacrylate)
TFE—tetrafluoroethylene
Tg—glass transition temperature
Tm—melting temperature
VAc—vinyl acetate

EXAMPLE 1

Preparation of
9,9-Dihydro-9-hydroxy-perfluoro-(3,6-dioxa-5-methyl-1-nonene)($CF_2=CFO-CF_2CF(CF_3)O-CF_2CF_2-CH_2OH$)

To a dry flask was charged EVE (211 g, 0.50 mole) in absolute ethanol (300 ml) with a magnetic stirring bar. Sodium borohydride (11.34 g, 0.30 mole) was added slowly from a solid addition funnel. The reaction was somewhat exothermic and the reaction pot was kept at $\leq 10°$ C. by external cooling. After the addition of sodium borohydride was completed, the reaction mixture was stirred for 1 hr at room temperature. The pot mixture was then dumped into an ice water (600 ml)/6N HCl (600 ml) mixture. The bottom product layer was separated, washed with water and distilled to give the desired product as a clear, colorless liquid. Bp, 68° C./25 mmHg. Yield: 168.7 g (85.6%). H-1 NMR(CDCl$_3$): 4.00 (dt, J=1.0 Hz, 13.5 Hz, 2H), 2.12 (s, br, 1H); F-19 NMR (CDCl$_3$, F-11 internal standard): $-80.4$ (s, br. 3F), $-84.2$ (s, br, 2F), $-85.3$ (m, br, 2F), $-126.6$ (t, J=14 Hz, 2F), $-145.7$ (t, J=21.8 Hz, 1F), $-113.4$, $-113.7$, $-113.8$, $-114.2$ (4 s, 1F), $-121.6$, $-112.1$, $-122.2$, $-122.7$ (4 t, J=5.2 Hz, 1F), $-135.3$, $-135.6$, $-135.9$, $-136.2$ (4 t, J=5.8 Hz, 1F).

EXAMPLE 2

Preparation of
9,9-Dihydro-9-hydroxyperfluoro-(3,6-dioxa-5-methyl-1-nonene)

EVE (21.1 g, 0.05 mole) was dissolved in absolute ethanol (15 ml) at 0° C. In a separate flask was charged sodium borohydride (1.15 g, 0.03 mole) in absolute ethanol (20 ml) at 0° C. The NaBH$_4$/EtOH solution as added slowly into EVE/EtOH solution while the pot temperature was kept between 0° to 5° C. After addition, the reaction mixture was stirred for 15 min at room temperature. The product was worked as described in Example 1 and distilled to give the clear, colorless product 11.7 g (59.4% yield) as a liquid. Bp. 70° C./25 mmHg.

EXAMPLE 3

Preparation of
7,7-Dihydro-7-Hydroxyperfluoro(3-Oxa-1-Heptene)($CF_2=CFO-CF_2CF_2CF_2-CH_2OH$)

To a dry flask was charged methyl perfluoro (5-oxa-6-heptenoate) (61.2 g, 0.2 mole) in absolute ethanol (120 ml). Sodium borohydride (4.54 g, 0.12 mole) was added slowly into the reaction solution via a solid additional funnel while the temperature was kept at about 10° C. The mixture was allowed to stir at room temperature for 1 hr after the addition of NaBH$_4$ was completed. The mixture was then dumped into ice water/6 NHCl (1:1 v/v, 500 ml) and worked up. The product was isolated by final distillation. 47.6 g (85.6% yield) of the desired product was obtained as a clear, colorless liquid. Bp. 54°–55° C./30 mmHg. H-1 NMR (CDCl$_3$): 4.10 (t, J=14.5 Hz, 2H); 2.65 (s, br, 1H); F-19 NMR (188.24 MHz, CDCl$_3$): $-85.7$ (m, 2F), $-123.4$ (m, 2F, $-127.6$ (s, br, 2F), $-113.7$, $-114.1$, $-114.2$, $-114.5$ (4 m, 1F), $-121.8$, $-122.3$, $-122.4$, $-122.9$ (4 t, J=5.6 Hz, 1F), $-134.9$, $-135.2$, $-135.5$, $-135.8$ (4 t, J=5.6 Hz, 1F).

EXAMPLE 4

Homopolymerization of
$CF_2=CFO-CF_2CF(CF_3)O-CF_2CF_2-CH_2OH$

Potassium t-butoxide (0.112 g, 0.001 mole) was dissolved in N,N-dimethyl formamide (DMF) (10 ml) and was cooled to 0° C. The title vinyl ether alcohol (7.88 g, 0.02 mole) in DMF (4 ml) was added slowly into the above solution via syringe. The reaction was maintained between at 10° to 25° C. via external cooling. After the addition was finished, the mixture was stirred for 2 hrs at about 10° C., then warmed up gradually to room temperature and was continued at ambient temperature for 6 hrs. The product mixture was dumped into ice water and was extracted with ether. The ether layer was separated, washed thoroughly with water and dried over magnesium sulfate. Ether solvent was removed in vacuo and the product polymer was further dried under high vacuum. 4.24 g (53.8% yield) of polymeric viscous oil was obtained. The weight average molecular weight was determined to be 4,100 with dispersion factor 1.51 by GPC with PMMA as the reference standard. The structure of the product was supported by its H-1 and F-19 NMR spectroscopic data.

EXAMPLE 5

Homopolymerization of
$CF_2=CFO-CF_2CF(CF_3)O-CF_2CF_2-CH_2OH$

The title vinyl ether alcohol (7.88 g, 0.02 mole) was polymerized with potassium t-butoxide (0.112 g, 0.001 mole) in DMF as described in Example 4. After warmed to room temperature, the reaction mixture was stirred at ambient temperature for 48 hrs instead of 6 hrs. After working up, the polymeric oil was determined to have weight average molecular weight, 5,920 with a dispersion factor 1.74 by GPC with PMMA as reference standard.

EXAMPLE 6

Homopolymerization of
$CF_2=CFO-CF_2CF_2CF_2-CH_2OH$

Potassium t-butoxide (0.112 g, 0.001 mole) was dissolved in DMF (10 ml) at 10° C. The alcohol substrate (5.56 g, 0.02 mole) in DMF (4 ml) was added slowly into the t-BuOK/DMF solution slowly via syringe. After stirring for 2 hrs at 10° C., the reaction mixture was warmed slowly to room temperature. Some exotherm was observed when temperature reached 25° C. The reaction mixture was cooled and kept stirring for 6 hrs at room temperature. The product was then dumped into ice water and was soaked up as previously described. 4.13 g (74.3% yield) of pale-yellow viscous polymeric oil was obtained. The weight average molecular weight of this polymer was determined to be 4,970 with dispersion factor 2.00 by GPC by the use of PMMA as the reference standard.

EXAMPLE 7

Free Radical Copolymerization of EVE Alochol with TFE

In a shaker tube was charged EVE Alcohol (10 g, 0.0254 mole), 1,1,2-trichloro-1,2,2-trifluoroethane (F-113) (60 g, 0.32 mole) and 4,4'-bis(t-butylcyclohexyl)-peroxy dicarbonate (0.05 g). The tube was sealed, cool-evacuated and tetrafluoroethylene (10 g, 0.1 mole) was then charged. The tube was sealed again and was heated at 50° C., 60° C. and 70° C. for 2 hrs respectively with shaking. The solvent was removed from the unloaded polymer solution and the polymer was finally dried in a vacuum oven (ca. 150 mmHg) at 120° C. for 24 hrs. White polymer, 9.0 g, was obtained. The polymer has a Tm at 240° C. as measured by DSC. The composition of this polymer was determined to be TFE/EVE alcohol=87/13 (mole %) by F-19 high temperature NMR spectroscopy.

EXAMPLE 8

Free Radical Copolymerization of EVE Alcohol with TFE

In the shaker tube was charged EVE alcohol (10 g, 0.0254 mole), F-113 solvent (20 g, 0.107 mole) and 4,4'-bis(t-butylcyclohexyl)peroxy dicarbonate (0.03 g). The tube was sealed and cool-evacuated and tetrafluoroethylene was charged in. The tube was heated to 45° C. and the pressure of tetrafluoroethylene maintained at 60 psi. The tube was shaken for 6 hrs and was worked up as in Example 7. 3.3 g of the white polymer was obtained. This polymer has shown a Tg at 164° C. as determined by DSC, and have a composition of TFE/EVE alcohol=74/26 (mole %) as determined by F-19 high temperature NMR spectroscopy.

EXAMPLE 9

Free Radical Copolymerization of EVE Alcohol and TFE

This polymerization as carried out with EVE alcohol monomer (4 g, 0.0102 mole), F-113 (72 g, 0.417 mole), 4,4'-bis(t-butylcyclohexyl)peroxy dicarbonate (0.05 g) and tetrafluoroethylene (20 g, 0.2 mole) in a shaker tube at 50° C., 2 hrs; 60° C., 2 hrs and 70° C., 2 hrs, 17.3 g of white polymer was obtained. The polymer has a Tm at 318.3° C. as shown by DSC and has a composition of EVE alcohol 98.5–99.0/1.5–1.0 (mole %) as determined by F-19 NMR.

EXAMPLE 10

Free Radical Copolymerization of EVE Alcohol and PDD

This polymerization was carried out with EVE alcohol (5 g, 0.0127 mole) and PDD (30 g, 0.123 mole) in F-113 (100 g, 0.533 mole) with 4,4'-bis(t-butylcyclohexyl)peroxy dicarbonate (0.06 g) initiator under the same temperature as described in Example 9. White polymer 6.3 g was obtained after workup. This polymer has a Tg at 210° C. The composition of this polymer was determined to be PDD/EVE alcohol=96.5/3.5, (mole %) by F-19 NMR.

EXAMPLE 11

Free Radical Copolymerization of EVE Alcohol, TFE and VAc

In the shaker tube was charged EVE alcohol (10 g, 0.0254 mole), VAc (40 g, 0.465 mole), F-113 (120 g, 0.64 mole) and 4,4'-bis(t-butylcyclohexyl)peroxy dicarbonate (0.1 g). The tube was sealed and tetrafluoroethylene (4 g, 0.04 mole) was added after the tube was cooled and evacuated. The tube was resealed and was heated at 60° C. for 6 hrs. The resulting polymer solution was dissolved in acetone and precipitated with ice water. The polymer was collected by filtration and washed with water and was dried under nitrogen purge at ambient temperature. White solid polymer 48.7 g was obtained. The polymer has a Tg at 40.6° C. by DSC and the polymer has a composition of VAc/TFE/EVE alcohol=62.8/27.6/9.6 (mole %) as calculated from its H-1 & F-19 NMR spectroscopic data. The structure of the polymer was also supported by its IR spectrum.

EXAMPLE 12

Free Radical Copolymerization of EVE Alcohol, TFE and PDD

This experiment was carried out with EVE alcohol (2 g, 0.0051 mole), PDD (51 g, 0.209 mole) and tetrafluoroethylene (1 g, 0.01 mole) in F-113 (165 g, 0.88 mole) by the use of 4,4'-bis(t-butylcyclohexyl)peroxy dicarbonate initiator (0.2 g) in a shaker tube at 50° C., 60° C. and 70° C. for 2 hrs respectively. 44.9 g of white polymer was obtained after working up. This polymer has shown a Tg at 224.3° C. by DSC.

Although preferred embodiments of the invention have been described hereinabove, it is to be understood that there is no attempt to limit the invention to the precise constructions herein disclosed, and it is to be further understood that the right is reserved to all changes coming within the scope of the invention as defined by the appended claims.

What is claimed is:

1. A copolymer comprising the hydroxy containing repeat unit

wherein:
p is 0 or 1;
m is 0 to 10; and
n is 1 to 20;
provided that when m is 0, p is 0, and
further provided that when m is greater than 0, p is 1; and
one or more other repeat units.

2. The copolymer as recited in claim 1 wherein said hydroxy containing repeat unit is about 0.001 to about 30 mole percent of the total repeat units in the copolymer.

3. The copolymer as recited in claim 1 wherein said hydroxy containing repeat unit is about 0.05 to about 15 mole percent of the total repeat units in the copolymer.

4. The copolymer as recited in claim 1 wherein at least one of said other repeat units is derived from a fluoromonomer.

5. The copolymer as recited in claim 1 wherein the said other repeat unit(s) are derived from monomers selected from the group consisting of tetrafluoroethylene; hexafluoropropylene and vinylidene fluoride; hexafluoropropylene and vinylidene fluoride and tetrafluoroethylene; ethylene and vinylidene fluoride; perfluoro(methyl vinyl ether) and tetrafluoroethylene; perfluoro(methyl vinyl ether) and hexafluoropropylene; chlorotrifluoroethylene; ethylene and chlorotrifluoroethylene; vinylidene fluoride; tetrafluoroethylene and propylene; tetrafluoroethylene and ethylene; tetrafluoroethylene and hexafluoropropylene; perfluoro-2,2-dimethyl-1,3-dioxole; perfluoro-2,2-dimethyl-1,3-dioxole and tetrafluoroethylene; vinyl fluoride; tetrafluoroethylene and perfluoro[2-(2-fluorosulfonylethoxy)propyl vinyl ether]; and vinyl acetate and tetrafluoroethylene.

6. The copolymer as recited in claim 1 wherein at least one of said other repeat units is derived from a vinyl ester.

7. The copolymer as recited in claim 6 wherein said vinyl ester is vinyl acetate.

8. The copolymer as recited in claim 1 wherein said other repeat units are derived from vinyl acetate and tetrafluoroethylene.

* * * * *